US00PP11970P2

(12) United States Plant Patent
Persoff

(10) Patent No.: US PP11,970 P2
(45) Date of Patent: Jul. 3, 2001

(54) MIMULUS PLANT NAMED 'JELLY BEAN APRICOT'

(76) Inventor: Richard Persoff, P.O. Box 2918, Alameda, CA (US) 94501

( * ) Notice: Subject to any disclaimer, the term of this patent is extended or adjusted under 35 U.S.C. 154(b) by 0 days.

(21) Appl. No.: 09/606,124

(22) Filed: Jun. 28, 2000

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Annette H. Para
(74) *Attorney, Agent, or Firm*—C. A. Whealy

(57) ABSTRACT

A distinct cultivar of Mimulus plant named 'Jelly Bean Apricot', characterized by its upright, somewhat open and relatively compact plant habit; freely branching habit; high vigor; dark green glossy leaves; and numerous large flowers that are initially pale yellow and become pink with development.

2 Drawing Sheets

BACKGROUND OF THE INVENTION

The present invention relates to a new and distinct cultivar of Mimulus plant, botanically known as *Mimulus aurantiacus*, and hereinafter referred to by the cultivar name Jelly Bean Apricot.

The new Mimulus is a product of a planned breeding program conducted by the Inventor in Alameda, Calif. The new Mimulus originated from a cross made by the Inventor of a proprietary selection of *Mimulus aurantiacus* identified as code No. B60-O15 as the female, or seed, parent with a proprietary selection of *Mimulus aurantiacus* identified as code No. K13-O13 as the male, or pollen, parent. The new Mimulus was selected in 1997 on the basis of its compact and freely flowering habit.

Asexual reproduction of the new cultivar by terminal cuttings taken at Alameda, Calif., has shown that the unique features of this new Mimulus are stable and reproduced true to type in successive generations.

SUMMARY OF THE INVENTION

Plants of the cultivar Jelly Bean Apricot have not been observed under all possible environmental conditions. The phenotype may vary somewhat with variations in environment such as temperature, light intensity, daylength, and nutritional status without, however, any variance in genotype.

The following traits have been repeatedly observed and are determined to be the unqiue characteristics of 'Jelly Bean Apricot'. These characteristics in combination distinguish 'Jelly Bean Apricot' as a new and distinct cultivar:

1. Upright, somewhat open and relatively compact plant habit.
2. Freely branching habit.
3. High vigor.
4. Dark green glossy leaves.
5. Numerous large flowers that are initially pale yellow and become pink with development.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Mimulus.

The photograph on the first sheet comprises a side perspective view of a typical flowering plant of 'Jelly Bean Apricot' grown in a 15-cm container.

The photograph at the top of the second sheet is a close-up view of typical flowering stems of 'Jelly Bean Apricot'.

The photograph at the bottom of the second sheet is a close-up view of typical flowers showing the progression of color changes with development and the upper and lower surfaces of typical leaves of 'Jelly Bean Apricot'.

DETAILED BOTANICAL DESCRIPTION

In the following description, color references are made to The Royal Horticultural Society Colour Chart except where general terms of ordinary dictionary significance are used. Plants grown in 15-cm containers were used for the following description with one plant per container. Plants were grown in polyethylene-covered greenhouses and under conditions which closely approximate commercial production conditions during the spring in Encinitas, Calif. Day temperatures averaged about 18° C., night temperatures averaged about 10° C., and light levels were about 5,000 to 6,000 foot-candles.

Botanical classification: *Mimulus aurantiacus* cultivar Jelly Bean Apricot.

Parentage:

*Female parent.*—Proprietary selection of *Mimulus aurantiacus* identified as code No. B60-O15, (unpatented).

*Male parent.*—Proprietary selection of *Mimulus aurantiacus* identified as code No. K13-O13, unpatented.

Propagation:

*Type cutting.*—Terminal vegetative cuttings.

*Time to initiate roots, summer.*—About 14 days at 20° C.

*Root description.*—Numerous, fine.

Plant description:

*Form.*—Mostly, upright, somewhat open plant habit; relatively compact.

*Usage.*—Appropriate for 15-cm containers.

*Crop time.*—About 18 weeks are required to produce finished flowering plants in 15-cm containers.

*Plant height.*—About 36 cm.

*Area of spread.*—About 30 cm.

*Vigor.*—Vigorous.

*Branching habit.*—Freely branching with about three lateral branches per plant; removal of terminal apices (pinching) enhances branching.

*Lateral branches.*—Length: About 28 cm. Diameter: About 3 mm. Internode length: About 5 cm. Texture: Slightly viscid; glabrous. Color: 144D.

*Foliage description.*—Leaves simple, generally symmetrical and long persisting; opposite. Quantity per lateral branch: Typically about 16 to 18. Width: About 2.2 cm. Length: About 7 cm. Aspect: Slightly reflexed. Shape: Elliptic. Apex: Rounded acute. Base: Attenuate. Margin: Entire. Texture: Viscid; glabrous; leathery. Color: Young foliage, upper surface: 147A to 147B; glossy. Young foliage, lower surface: 147B. Mature foliage, upper surface: 147A to 147B; glossy, venation, 147B. Mature foliage, lower surface: 147B; venation, 147C. Petiole: Length: About 5 mm. Diameter: About 4.5 mm. Color: 147C.

Flower description:

*Flower type and habit.*—Large-sized flowers; flowers face mostly outward; single, axillary; salverform, zygomorphic. Flowers persistent.

*Natural flowering season.*—Flowering typically from early spring until fall; about 10 weeks from planting to flowering.

*Quantity.*—Freely and continuous flowering; typically about 70 flower buds and opened flowers per plant.

*Fragrance.*—Not detected.

*Flower longevity on the plant.*—About 3 days.

*Flower buds* (*showing color*).—Length: About 3.5 cm. Diameter: About 1.2 cm. Shape: Elongate. Color: 18A.

*Corolla.*—Arrangement/appearance: Five-parted, fused into a tube; lobes, flared. Flower diameter: Vertical axis, about 5 cm; horizontal axis, about 4.5 cm. Flower depth (length): About 5 cm. Flower tube length: About 4.2 cm. Petal length: About 5 cm. Petal width: About 1.25 cm. Petal shape: Fan-shaped; lobes irregularly cordate or sinuate, slightly reflexed and appear slightly ruffled. Texture: Smooth, satiny. Color: Petal, upper surface, when opening: Pale yellow, 18A, with pale orange, 32C, striations at base of petal lobes towards throat. Petal, lower surface, when opening: Pale yellow, 18B, with reddish, 179A, blush. Petal, upper surface, opened flower: Pale pink, 49C to 49D, with darker pink, 54C, striations at opening of throat; lobes subsequently becoming slightly more orange, 36A. Petal, lower surface, opened flower: Pink, 39C, tinged with pale yellow, 18A. Flower throat (inside): Pale yellow, initially 19C darkening to 18A with development. Flower tube (outside): Proximal to distal, 38A to 38B to 38C.

*Sepals.*—Quantity: Five, fused. Shape: Elliptic; folded at midveins; calyx, zygomorphic tube. Calyx length: About 2.5 to 3 cm. Calyx diameter: About 1 cm. Apex: Acute. Margin: Entire. Texture: Smooth; viscid. Color: Upper surface: 144B. Lower surface: 144A.

*Peduncle.*—Strength: Good. Angle: Somewhat upright to nearly horizontal, about 60 to 90° to the stem. Length: About 5 mm. Color: 144B.

*Reproductive organs.*—Stamens: Quantity: Four total, two shorter than the other two. Anther shape: Ovoid. Anther size: About 2 by 1 mm. Anther color: 161B. Pollen amount: Scarce. Pollen color: 158A. Pistils: Pistil quantity per flower: One. Pistil length: About 4 cm. Stigma shape: Anvil-shaped, becoming tri-lobed. Stigma color: 155A. Style length: About 3.3 cm. Style color: 155A. Ovary color: 144B.

*Seed.*—Seed production has not been observed.

Disease resistance: Plants of the new Mimulus have not been noted to be resistant to pathogens common to Mimulus.

It is claimed:

1. A new and distinct cultivar of Mimulus plant named 'Jelly Bean Apricot', as illustrated and described.

* * * * *

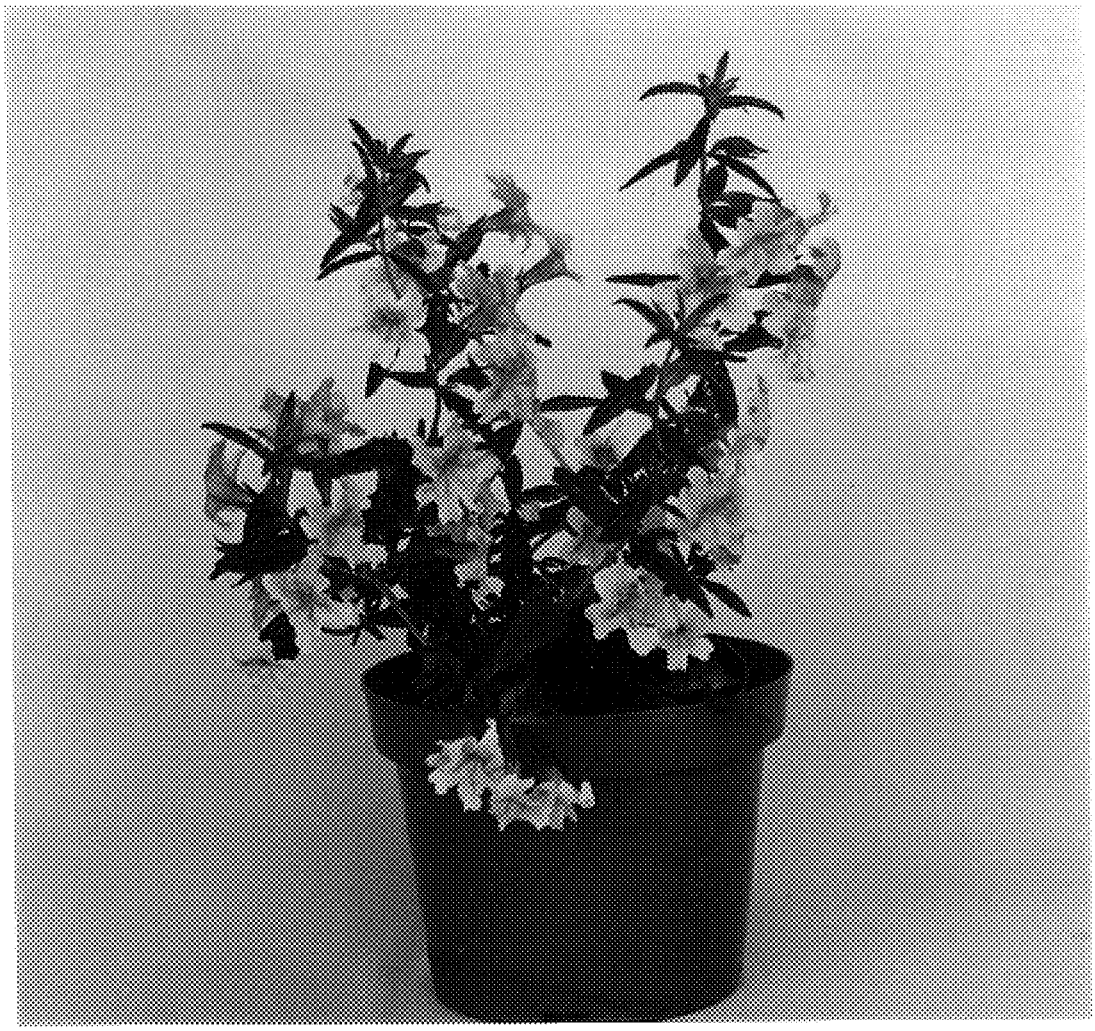

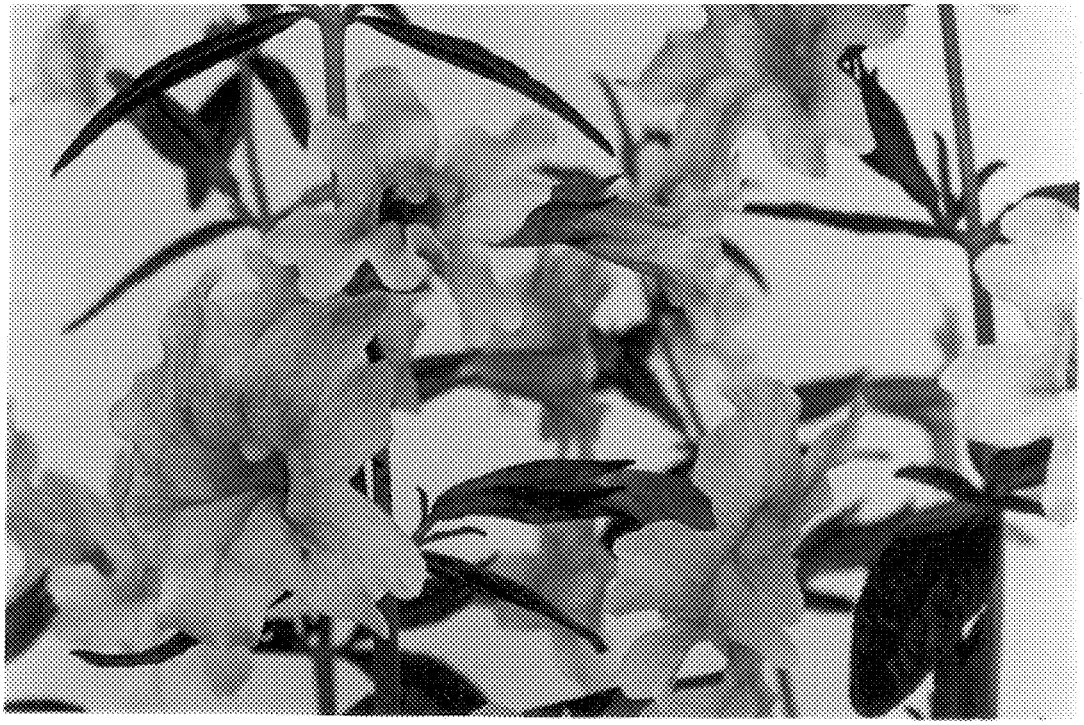
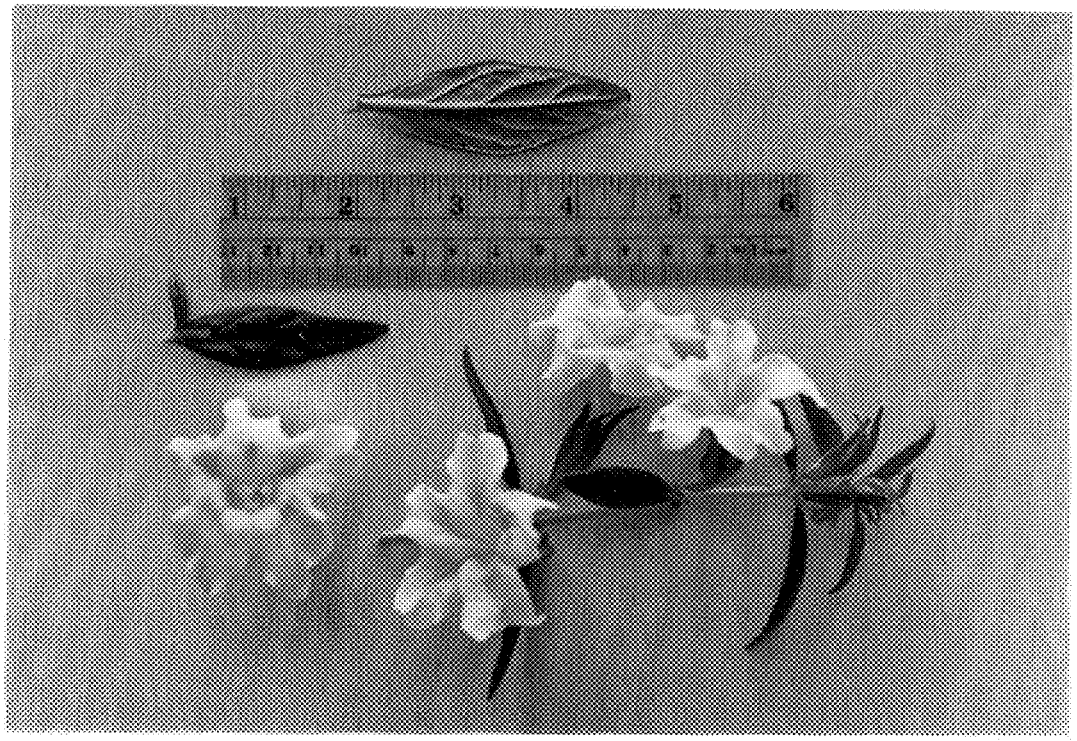
1
2
3
4
5
6